United States Patent [19]

Lake

[11] 4,033,342

[45] July 5, 1977

[54] NASAL PROTECTIVE SPLINT

[76] Inventor: Norman M. Lake, 1705 Newport Drive, Lancaster, Pa. 17602

[22] Filed: Sept. 5, 1975

[21] Appl. No.: 610,655

[52] U.S. Cl. .............................. 128/140 N; 128/346
[51] Int. Cl.² ........................................ A61M 16/00
[58] Field of Search ....... 128/132 R, 145 A, 145 R, 128/133, 142, 142.2, 147, 203, 346

[56] References Cited

UNITED STATES PATENTS

| 540,629 | 1/1900 | Carence | 128/140 N |
| 580,954 | 4/1897 | Ray | 128/76 C |
| 690,663 | 1/1902 | Pratt | 128/145 A |
| 2,011,733 | 8/1935 | Shindel | 128/146 |
| 2,015,617 | 9/1935 | Claudius | 128/346 |
| 2,064,986 | 12/1936 | Mezz | 128/132 R |
| 2,153,487 | 4/1939 | Schwartz | 128/146 |
| 2,274,997 | 3/1942 | Thurman | 128/132 |
| 2,317,236 | 4/1943 | Wilen et al. | 128/145 A |
| 2,323,199 | 6/1943 | Bulbulian | 128/146 |
| 2,620,793 | 12/1952 | Gollubier | 128/132 R |
| 2,757,665 | 8/1956 | Tanikawa | 128/76 C |

*Primary Examiner*—Robert W. Michell
*Assistant Examiner*—Henry J. Recla
*Attorney, Agent, or Firm*—Jackson, Jackson & Chovanes

[57] ABSTRACT

Nasal protection for the nostrils comprising a U-shaped wire-spring having an ellipsoidal-like nub fastened to each end for pressing the nostrils.

2 Claims, 5 Drawing Figures

U.S. Patent  July 5, 1977  4,033,342
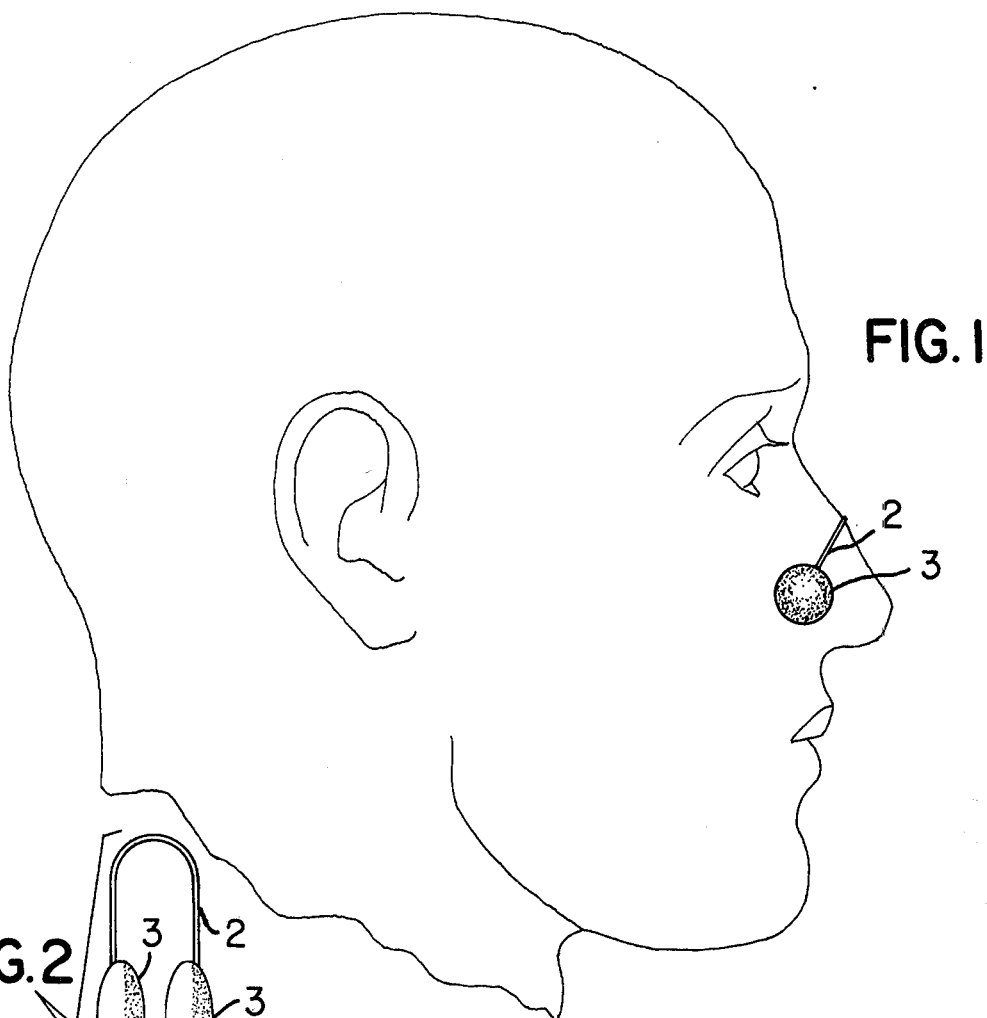
FIG.1
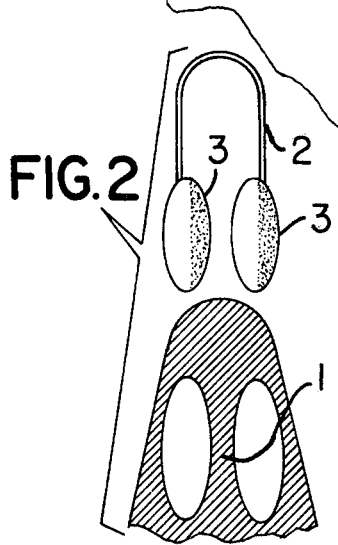
FIG.2
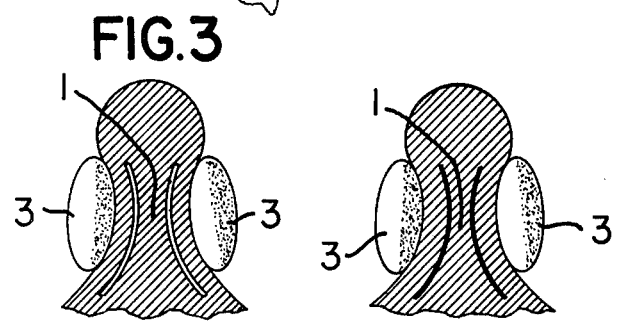
FIG.3
FIG.4
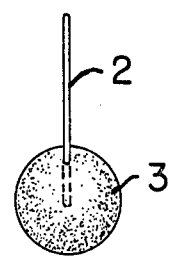
FIG.5

NASAL PROTECTIVE SPLINT

DESCRIPTION OF THE INVENTION

This invention relates to an improvement in nasal protectors and has for its object the protection of the mucous membranes of the nasal passages. To this end inhalation of airborne irritants into the nasal passages are trapped or minimized, and reactions to a stimulus (which are manifested by sneezing) are inhibited.

Toward this objective (1) thenostrils of the individual are closed to a degree sufficient to trap or minimize inhalation of airborne irritants into the nose and insufficient to block breathing and watery secretions therefrom; and (2) the explosive actions of sneezing are inhibited by control of voluntary muscles of the nose, thus precluding or abating the inflammatory process, whereby the attendant evils therefrom are arrested or alleviated.

The means employed of carrying out this invention include a small U-shaped nasal splint comprising a small resilient and adjustable-wire sring (ranging in diameter 0.035 of an inch) to each end of which is attached a solid (called a nub) generated by revolving an elliptic-like plane section through 180°. The nubs are preferably of plastic having the legs of the spring attached thereto in an off-center position, thus adapting the splint to a nose of wider shape without having to increase the thickness of the nubs thereby resulting in a saving of material and improving its appearance when in use.

During the fall, winter and spring seasons particularly, the nasal mucous membranes of the individual are subjected to attack by countless airborne irritants which are constantly being breathed into the nose, some of which are often infectious. Many of these agents, after entering the nose, are conveyed by the mucous blanket back to the throat where they are swallowed and rendered harmless. But unfortunately, some succeed in escaping this movement to the throat and instead land in and attack the membranes. Irritation then begins and evils generate and develop. When this condition is reached, the individual soon succumbs to the explosive actions of sneezing — and as sneezing is well known to irritate the nasal mucous membranes — the problem then becomes compounded, causing a rapid development of the inflammatory process which results in nasal blockage and in other complications. When an irritating agent attacks the nasal mucosa, irritation therefrom ensues. Two things then promptly occur, (1) the small vessels of the nasal membranes dilate and watery secretions therefrom are increased, and (2) nature reacts to this irritation by sneezing which appears to be nature's way of removing the agent that is causing the irritation. If the causative agent is non-infectious, sneezing will often dislodge it and the secretions, which are part of nature's defense cycle, can wash it back in the throat to be swallowed. However, the non-infectious invader can often become so entrenched in the nasal mucosa that sneezing will fail to dislodge it, and along with its continued irritation coupled with that from sneezing, complications can surely be expected to follow. If, on the other hand, the irritation is being caused by an infectious agent, a different situation develops, that is, the agent has succeeded in gaining entrance to a living cell from which it gains protection from being dislodged by sneezing. So here again, an invader is inflicting irritation and setting the stage for complications to follow, which in this case are perhaps more serious. In both of these cases, irritation of the nasal passages causes the inflammatory process to develop, resulting in nasal blockage and other disorders, but when the inflammatory process is caused by an infectious agent, favorable conditions are thereby created under which this infectious agent may multiply and produce results that are injurious.

An object of this invention is first of all to bar or reduce to a minimum the inhalation of irritating agents into the nose; and secondly, to inhibit the reactions to these irritants which escape the mucous blanket and initiate irritation in the nasal mucosa. In the performance of these functions, the nasal splint is employed and as its wire-spring is both resilient and flexible, and adaptability to any shape and size of nose is provided. It is well known that individuals tend to hold and pinch the nose in an effort to stop sneezing but have little or no success. All that is achieved is recovery of the nasal discharge. This practice is insufficient to overcome sneezing. I have discovered from actual experience that to successfully inhibit those explosive actions, not only must a firm pressure be exerted on the nasal septum for two to three minutes, but also at the same time forceful attempts to inhale through the nose must be exercised. This dual process proved to be the key to controlling the voluntary muscles of the nose.

Hence, when repeated spells of sneezing occur, the nasal splint should be adjusted to exert a firm pressure on the nasal septum, and while holding this position for 2 or 3 minutes, forceful attempts to inhale through the nose should be exercised. At the end of the period when sneezing most likely will have been overcome, adjust the splint to a degree only sufficient to breathe comfortably through the nose yet retain a degree of constriction in the nasal passages. In this adjusted position of the nasal splint, it will trap or minimize inhalation of irritants into the nose, and it can be worn as long as desired with safety and little or no discomfort.

It should be noted that when the nasal mucous membranes are under attack, watery secretions of the nose occur. By actual experience I have discovered that blotting these secretions rather than blowing the nose has proved most helpful toward achieving the objective of the invention. Furthermore, use of this nasal splint will operate as a deterrent to nose blowing.

Prior art shows various devices to be worn on the nose for multiple purposes, none of which teaches the use of this invention, and in their operation a health hazard is involved either by clamping or sealing the nose especially from the outside atmosphere for prolonged periods of time. In fact, it is well known that blockage of the nose for prolonged periods tends to infect the accessory sinuses.

This invention resides not merely in using a nasal clip, but in making a nasal protective splint adaptable for a new and inventive use. The prime object of the invention is to fulfill a health need long desired but never attained which fact is manifested by its absence of availability for public benefit. My invention is novel since it is out of the ordinary and unobvious because it is insufficiently evident as to arrest attention.

The nasal splint has striking properties over conventional nasal protective devices, namely, (1) practicability (more acceptable for public use); (2) less unsightly to wear; (3) comfortable to wear; (4) no health hazard; (5) manufacturing costs will be at a minimum since it comprises only two simple parts; (6) a lower price level can be created by making volume production easier.

In this application the following drawings are filed:

FIG. 1 illustrates a nasal splint in use.

FIG. 2 is a cross section illustrating open nostrils prior to applying the nasal splint.

FIG. 3 is a cross section illustrating the nasal splint positioned on the nose for long periods in use with the nostrils closed to the degree as set forth in the specification.

FIG. 4 shows a cross section illustrating the splint positioned on the nose completely closing the nostrils and exerting firm pressure on the nasal septum as set forth in the specification.

FIG. 5 shows a front elevation of a nasal splint.

FIG. 1 illustrates the wire-spring 2 and the nasal nub 3, which are fastened by insertion of spring end into nub.

FIGS. 2, 3 and 4 show the septum 1.

The wire-spring 2, an inverted U in shape, has the ends of the arms of its inverted U inserted into the tops of the ellipsoid-like nub at points slightly outside the central vertical axis of the ellipsoidal cross-section in each case. The gap between the inner faces of the nubs will range from 0.3 to 0.4 of an inch when not in use.

The combination of these two is shown in FIG. 5.

In view of my invention and disclosure, variations and modifications to meet individual whim or particular need will doubtless become evident to others skilled in the art to obtain all or part of the benefits of my invention without copying the structure shown, and I therefore claim all such insofar as they fall within the reasonable spirit and scope of my claims.

NOTE: When reference is made to the nostrils throughout this application, it is intended to include the area of the nasal passages from the external nares to the upper bony cartilage of the nose.

Having thus described my invention, what I claim as new and desire to secure by Letters Patent is:

1. A new process of employing a particular nasal splint for helping the human nose maintain its mucous membranes in good condition, said splint comprising a U-shaped wire spring for straddling the nose and having two nubs each circular in outline with two convex side faces, each leg of the U-shaped spring being embedded in a different one of the nubs, said nubs being biased towards each other by said spring, said process comprising locating the splint such that the spring of the splint presses the nubs in on the sides of the nose in the area defined by the portion above the alae and by the upper portion of the alae, this being done to a degree sufficient to trap or minimize inhalation of airborne irritants into the nose, but insufficient to block breathing and watery secretions therefrom, thus helping the human nose protect against the numerous irritants breathed into the nose during certain seasons of the year.

2. A new process of employing a particular nasal splint for helping the human nose maintain its mucous membranes in good condition, said splint comprising a U-shaped wire spring for straddling the nose and having two nubs, each circular in outline with two convex side faces, each leg of the U-shaped spring being embedded in a different one of the nubs, said nubs being biased towards each other by said spring, and said process comprising locating the splint such that the spring of the splint presses the nubs in on the sides of the nose in an appropriate area defined by the portion above the alae and by the upper portion of the alae, this being done to the extent of closing off the nasal passages and exerting a firm pressure on the septum for a period of 2 or 3 minutes during which time forceful attempts to inhale through the nose will be exercised thus helping control the compound explosive reactions of sneezing and thereby precluding or abating the inflammatory process whereby the attendant evils therefrom are arrested or alleviated, relocating said splint with respect to the nose such that the spring of the splint presses the nubs in on the sides of the nose in the area defined by the portion above the alae and by the upper portion to a degree sufficient to trap or minimize inhalation of airborne irritants into the nose, but insufficient to block breathing and watery secretions therefrom, thus helping the human nose protect against the numerous irritants breathed into the nose during certain seasons of the year.

* * * * *